United States Patent [19]

Gleixner et al.

[11] 4,189,469

[45] Feb. 19, 1980

[54] PHARMACEUTICAL COMPOSITIONS

[75] Inventors: Klaus Gleixner, Taunusstein-Wehen; Roland Müller; Franz Lehrach, both of Wiesbaden, all of Fed. Rep. of Germany

[73] Assignee: Hoechst Aktiengesellschaft, Frankfurt, Fed. Rep. of Germany

[21] Appl. No.: 683,795

[22] Filed: May 6, 1976

[30] Foreign Application Priority Data

May 10, 1975 [DE] Fed. Rep. of Germany ....... 2520978

[51] Int. Cl.$^2$ ..................... A61K 31/79; A61K 31/70; A61K 31/52; A01N 17/00
[52] U.S. Cl. ........................................ 424/80; 424/10; 424/78; 424/180; 424/253
[58] Field of Search ..................... 424/19, 253, 10, 78, 424/80, 180

[56] References Cited

U.S. PATENT DOCUMENTS

| | | | |
|---|---|---|---|
| 3,065,143 | 11/1962 | Christenson et al. | 424/19 |
| 3,577,514 | 5/1971 | Robinson | 424/19 |
| 3,590,117 | 6/1971 | Christenson et al. | 424/19 |
| 3,639,169 | 2/1972 | Broeg et al. | 424/157 |
| 3,864,469 | 2/1975 | Reiser et al. | 424/19 |

OTHER PUBLICATIONS

Ritschel–*Die Tablette,* Editio Cantor KG/Aulendorf i Württ, pp. 93, 191–193.

*Primary Examiner*—Frederick E. Waddell
*Attorney, Agent, or Firm*—Berman, Aisenberg & Platt

[57] ABSTRACT

A pharmaceutical composition for oral administration in dosage unit form which comprises at least one xanthine derivative selected from the group consisting of (a) (ω-1(-hydroxyalkyl-dialkylxanthines wherein the (ω-1)-hydroxyalkyl group contains 5 or 6 carbon atoms and is in the 1- or 7-position, the alkyl group in the other of the 1- and 7-position contains from 1 to 12 carbon atoms and the alkyl group in the 3-position contains from 1 to 4 carbon atoms,
(b) (ω-1)-oxoalkyl-dimethylxanthines wherein the (ω-1)-oxoalkyl group contains 5 or 6 carbon atoms and is in the 1- or 7-position,
(c) dimethylxanthine derivatives having an additional alkyl group containing from 4 to 12 carbon atoms in the 1- or 7-position, and
(d) dimethylxanthine derivatives having an additional benzyl group in the 1- or 7-position and a saliva forming agent, each dosage unit containing at least 300 mg of xanthine derivative, and the weight ratio of xanthine derivative to saliva forming agent being in the range from 1:2 to 10:1 and a method for the preparation of said composition.

18 Claims, No Drawings

PHARMACEUTICAL COMPOSITIONS

This invention relates to pharmaceutical compositions for oral administration containing xanthine derivatives.

It is well known that certain pharmaceutically active compounds, e.g. xanthine derivatives, particularly dimethylxanthines and derivatives thereof, have a rather high incompatibility with the gastro-intestinal tract. Pharmaceutical products containing these compounds are thus frequently presented in the form of injection solutions, solution for infusion or coated tablets resistant to gastric juices. In the latter pharmaceutical form, the dosage has had to be kept low to avoid incompatibility reactions and this has heretofore restricted the usefulness of oral therapy.

The irritant effect on the gastric mucous membrane is particularly strong when larger quantities of the active ingredient are released in and come into contact with a narrowly circumscribed area of the musous membrane, as is the case, for example, when a tablet rests on the gastric mucous membrane and decomposes there within a short time, e.g. in about 1 to 2 minutes. The problem is only partially solved by administration of pharmaceutical preparations which are resistant to gastric juices, since the decomposition of the pharmaceutical form does not then take place until it reaches the small intestine. Moreover, with subacid and anacid patients, the pharmaceutical preparation nevertheless decomposes in the stomach itself. For the reasons described above, the use of oral therapy with certain pharmaceuticals, which is generally preferred because of its convenience, has been severely restricted because of the limitations imposed by the low dosage levels which can be administered safely.

Pharmaceutical compositions for oral administration may be produced by granulating the active ingredient with the excipients, e.g. lactose or cane sugar, to produce a fairly coarse granulate which, after further granulation is compressed into tablets. It is also possible to compress a powder mixture with a moisture content of 3 to 6% directly into tablets.

The present invention is based upon the discovery that the incompatibility of certain pharmaceuticals with the gastro-intestinal tract may be considerably reduced by admixture of the pharmaceutical with a sufficient amount of a saliva forming agent, thereby permitting safe oral administration of such pharmaceuticals in considerably higher dosages than has been possible heretofore.

Thus according to the present invention there is provided a pharmaceutical composition for oral administration in dosage unit form which comprises at least one xanthine derivative selected from (a) ($\omega$-1)-hydroxyalkyl-dialkylxanthines wherein the ($\omega$-1)-hydroxyalkyl group contains 5 or 6 carbon atoms and is in the 1- or 7-position, the alkyl group in the other of the 1- and 7-positions contains from 1 to 12 carbon atoms and the alkyl group in the 3-position contains from 1 to 4 carbon atoms;

(b) ($\omega$-1)-oxoalkyl-dimethylxanthines wherein the ($\omega$-1)-oxoalkyl group contains 5 or 6 carbon atoms and is in the 1- or 7-position; and (c) dimethylxanthine derivatives having an alkyl group containing from 4 to 12 carbon atoms or a benzyl group in the 1- or 7-position, and a saliva forming agent, each dosage unit containing at least 300 mg, preferably at least 400 mg, of xanthine derivative and the weight ratio of xanthine derivative to saliva forming agent being in the range of from 1:2 to 10:1, preferably from 1:1 to 6:1.

The invention is particularly valuable for administration of water-soluble xanthine derivatives but is also useful for administration of xanthine derivatives which are not soluble in water. The invention makes it possible for pharmaceutically active compounds which are water-soluble and badly tolerated by the stomach to be administered orally in considerably higher doses than has been possible heretofore, whilst avoiding incompatibility reactions in the gastro-intestinal tract. This has been demonstrated as follows:

Where 400 mg of 1-(5-oxohexyl)-3,7-dimethylxanthine were administered together with carries and excipients, but without a saliva forming agent, the level of this active ingredient in the blood was found to rise rapidly but then fall again very rapidly. This indicates that the substance is well resorbed and quickly eliminated by the body.

In contrast, where 400 mg of the same active ingredient were administered in the form of a pharmaceutical composition according to the invention, a relatively constant level of the active ingredient was sustained in the blood for a long period. This indicated a gradual release of the active ingredient from the pharmaceutical composition. Although decomposition products of the active ingredient are constantly eliminated in the urine, the level of active ingredient in the blood remained relatively constant over a long period. This thus confirms that there is a constant release of the active ingredient after resorption from the gastro-intestinal tract.

In tests carried out in vitro we have shown that constant quantities of the active ingredient are also released per hour into artificial gastric and intestinal juices.

Such in vitro and in vivo tests show that a constant level of the active ingredient is resorbed from the compositions according to the invention over a long period in the gastro-intestinal tract, thus guaranteeing a long-lasting therapeutic effect.

By means of the invention it is generally possible to administer safely the aforementioned xanthine derivatives in the form of individual dosage units containing up to 800 mg of active ingredient.

Typical water-soluble oxoalkyl-dialkylxanthines which may be incorporated into pharmaceutical compositions according to the invention include for example 1-(5-oxohexyl)-3,7- and 7-(5-oxohexyl)-1,3-dimethylxanthines. Other suitable xanthines are for example 3,7-dimethylxanthines and 1,3-dimethylxanthines substituted by a butyl, isoamyl, hexyl, lauryl or benzyl group in the 1- or 7-position, and also homologues of these compounds with a hydroxy or oxo group in the ($\omega$-1)-position, e.g. 1-(4-hydroxypentyl)- and 1-(5-hydroxyhexyl)-3,7-dimethylxanthines, 7-(4-hydroxypentyl)- and 7-(5-hydroxyhexyl)-1,3-dimethylxanthines, 1-(4-oxopentyl)-, 1-(5-oxohexyl)-, 1-(2-methyl-3-oxobutyl)- and 1-(2-ethyl-3-oxobutyl)-3,7-dimethylxanthines and the corresponding 1,3-dimethyl compounds having the aforementioned ($\omega$-1)-hydroxyalkyl or ($\omega$-1)-oxoalkyl groups in the 7-position. Suitable homologues of the above hydroxyalkyl-dimethylxanthines, are those having in the 1- or 7-position which is not occupied by a hydroxyalkyl group, instead of a methyl group, an alkyl group with 2 to 12 carbon atoms, e.g. 1-ethyl-, 1-propyl- , 1-butyl- and 1-isobutyl-3-methyl-7-(5-hydroxyhexyl)-xanthines and 7-ethyl-, 7-propyl-, 7-butyl- and 7-isobutyl-1-(5-hydroxyhexyl)-3-methylxanthines, and corresponding compounds having in place of the 3-methyl group an alkyl group with 2 to 4 carbon atoms.

The saliva forming agent, which generally also acts as a swelling agent, is preferably guar powder, a galactomannane, an alginate, an acrylic acid polymer, for example the commercial product Carbopol, or a cellulose derivative, for example methyl cellulose or more especially hydroxyethyl cellulose.

Further excipients, for example polyvinyl pyrrolidone, mixtures of polyvinyl pyrrolidone with polyvinyl acetate, talc, magnesium stearate and other excipients conventionally used in tablet making, may be incorporated into the compositions as desired.

Compositions according to the invention in the form of tablets and tablet cores may be prepared by the following method, which method constitutes a further feature of the invention: admixing one or more xanthine derivatives as hereinbefore defined with a saliva forming agent in a weight ratio of xanthine derivative to saliva forming agent of from 1:2 to 10:1 preferably from 1:1 to 6:1, granulating the mixture thereby produced and compressing the granulate into tablets or tablet cores each containing at least 300 mg, preferably at least 400 mg, of xanthine derivative.

One or more further excipients may be incorporated into the compositions prior to, during or after granulation as convenient. Where tablet cores are produced, these can be subsequently coated as desired to prepare coated tablets.

Granulation is preferably carried out as a dry granulation. However, other conventional granulation processes may also be used.

By means of the compositions according to the invention, it is safe to administer orally the aforespecified xanthine derivatives in the form of solid dosage units having an active ingredient content which is at least twice as high, often from 3 to 6 times as high as the highest dosages of the same active ingredient administered hitherto. In individual cases, the dosage which may be safely administered may even be 8 times as high.

When a pharmaceutical composition according to the invention is swallowed and comes into contact with water or gastric juices it is thought that a mucous layer is spontaneously formed around it which layer protects the mucous membrane from the direct action of the high concentration of active ingredient. When we tested pharmaceutical compositions according to the invention containing certain oxoalkyldialkylxanthines on humans, we found that dosages of at least 400 mg, generally from 800 to 1200 mg, and even as much as 2400 mg could be administered daily without the occurrence of any incompatibility reactions. The xanthine derivatives with which this invention is concerned are used particularly in the treatment of blood flow disorders and develop an optimum activity at individual single dosage levels above 300 mg. Such dosages could previously only be administered by infusion but as a result of the present invention may now be administered by the more convenient oral route.

The following Examples serve to illustrate the preparation of pharmaceutical compositions according to the invention.

EXAMPLES

In each case the various ingredients were admixed, agglomerated in a compactor, granulated and subsequently compressed into tablets or cores for coated tablets having the indicated compositions:

EXAMPLE 1

(a) 400 mg of 1-(5-oxohexyl)-3,7-dimethyl-xanthine
(b) 80 mg of hydroxyethyl cellulose
(c) 10 mg of polyvinylpyrrolidone
(d) 20 mg of talc
(e) 5 mg of magnesium stearate

EXAMPLE 2

(a) 300 mg of 1-propyl-3-methyl-7-(5-hydroxyhexyl)-xanthine
(b) 200 mg of hydroxyethyl cellulose
(c) 20 mg of polyvinylpyrrolidone
(d) 10 mg of talc
(e) 5 mg of magnesium stearate

EXAMPLE 3

(a) 400 mg of 1,3-dimethyl-7-(4-hydroxypentyl)-xanthine
(b) 100 mg of hydroxyethyl cellulose
(c) 20 mg of polyvinylpyrrolidone
(d) 10 mg of talc
(e) 5 mg of magnesium stearate

EXAMPLE 4

(a) 400 mg of 1-(5-hydroxyhexyl)-3,7-dimethylxanthine
(b) 100 mg of hydroxyethyl cellulose
(c) 20 mg of polyvinylpyrrolidone
(d) 10 mg of talc
(e) 5 mg of magnesium stearate

EXAMPLE 5

(a) 500 mg of 1-pentyl-3,7-dimethylxanthine
(b) 50 mg of hydroxyethyl cellulose
(c) 5 mg of polyvinylpyrrolidone
(d) 15 mg of talc
(e) 5 mg of magnesium stearate

EXAMPLE 6

(a) 800 mg of 1-hexyl-3,7-dimethylxanthine
(b) 150 mg of guar powder
(c) 20 mg of polyvinylpyrrolidone
(d) 15 mg of talc
(e) 5 mg of magnesium stearate.

EXAMPLE 7

(a) 800 mg of 1-(5-oxohexyl)-3,7-dimethylxanthine
(b) 150 mg of guar powder
(c) 20 mg of talc
(d) 5 mg of magnesium stearate It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:

1. An orally-administrable pharmaceutical composition in unit-dosage form which comprises an amount of pharmaceutically-active component having a degree of gastro-intestinal-tract incompatibility which renders it unsafe for oral administration in combination with a sufficient amount of swelling agent to reduce such incompatibility to a level at which the unit dosage is safe for oral administration.

2. A pharmaceutical composition as claimed in claim 1 for oral administration in dosage unit form which comprises at least one xanthine derivative selected from the group consisting of
  (a) (107 -1)-hydroxyalkyl-dialkylxanthine wherein the (ω-1)-hydroxyalkyl group contains 5 to 6 carbon atoms and is in the 1- or 7-position, the alkyl group in the other of the 1- and 7-positions contains from 1 to 12 carbon atoms, and the alkyl group in the 3-position contains from 1 to 4 carbon atoms,
  (b) (ω-1)-oxoalkyl-dimethylxanthine wherein the (ω-1)-oxoalkyl group contains 5 to 6 carbon atoms and is in the 1- or 7-position,
  (c) dimethylxanthine derivative having an additional alkyl group containing from 4 to 12 carbon atoms in the 1- or 7-position, and
  (d) dimethylxanthine derivative having an additional benzyl group in the 1- or 7-position
and a swelling agent, each dosage unit containing at least 300 mg of xanthine derivative, and the weight ratio of xanthine derivative to swelling agent being in the range from 1:2 to 10:1.

3. A composition as claimed in claim 2 wherein the xanthine derivative is water-soluble.

4. A composition as claimed in claim 2 wherein each dosage unit contains at least 400 mg of xanthine derivative.

5. A composition as claimed in claim 2 wherein each dosage unit contains up to 1200 mg of an (ω-1)-oxoalkyl-dimethylxanthine.

6. A composition as claimed in claim 2 wherein the xanthine derivative comprises 1-(5-oxohexyl)-3,7-dimethylxanthine or 7-(5-oxohexyl)-1,3-dimethylxanthine.

7. A composition as claimed in claim 2 wherein the swelling agent is a member selected from the group consisting of guar powder, galacto-mannane, an alginate, an acrylic acid powder and a cellulose derivative.

8. A composition as claimed in claim 2 which additionally contains a further excipient selected from the group consisting of polyvinyl pyrrolidone, polyvinyl acetate, talcum and magnesium stearate.

9. A composition as claimed in claim 2 in tablet form.

10. A pharmaceutical composition as claimed in claim 2 wherein the xanthine derivative is in admixture with the swelling agent.

11. A composition as claimed in claim 2 wherein the xanthine derivative is 1-(5-hydroxyhexyl)-3,7-dimethylxanthine.

12. A composition as claimed in claim 2 wherein the xanthine derivative is 7-(5-hydroxyhexyl)-1,3-dimethylxanthine.

13. A pharmaceutical composition as claimed in claim 2, which is safe for oral administration in dosage unit form and wherein the xanthine derivative is (a).

14. A pharmaceutical composition as claimed in claim 2, which is safe for oral administration in dosage unit form and wherein the xanthine derivative is (b).

15. A pharmaceutical composition as claimed in claim 2, which is safe for oral administration in dosage unit form and wherein the xanthine derivative is (c).

16. A pharmaceutical composition as claimed in claim 2, which is safe for oral administration in dosage unit form and wherein the xanthine derivative is (d).

17. In a method for preparing a pharmaceutical composition in oral dosage form with a pharmaceutically-active component having a degree of gastro-intestinal-tract incompatibility which renders in unsafe for oral administration, the improvement which comprises admixing the pharmaceutically-active component with a sufficient amount of swelling agent to reduce such incompatibility to a level at which the pharmaceutical composition is safe for oral administration.

18. In a method for preparing a pharmaceutical composition in oral unit-dosage form with a pharmaceutically-active component having a degree of gastro-intestinal-tract incompatibility which renders it unsafe for oral administration in excess of a particular unit dosage, the improvement which comprises admixing a higher unit dosage of the pharmaceutically-active component with a sufficient amount of swelling agent to reduce such incompatibility to a level at which the oral unit-dosage form with the higher unit dosage is safe for oral administration.

* * * * *

UNITED STATES PATENT AND TRADEMARK OFFICE
CERTIFICATE OF CORRECTION

PATENT NO. : 4,189,469
DATED : February 19, 1980
INVENTOR(S) : Klaus Gleixner and Roland Müller It is certified that error appears in the above-identified patent and that said Letters Patent are hereby corrected as shown below:

```
Title page, in the Abstract, line 4, "(ω-1(-hydroxyalkyl"
                    should read --(ω-1)-hydroxyalkyl--.
Column 1, line 21, "musous" should read --mucous--.
Column 2, line 18, "carries" should read --carriers--;
          lines 57 and 58, clarify --hydroxyhexyl--.
Column 5, line 10, "(107 -1)-hydroxyalkyl" should read
                    --(ω-1)-hydroxyalkyl--;
          line 11, "to" should read --or--;
          line 17, "to" should read --or--.
Column 6, line 28, "in" should read --it--.
```

Signed and Sealed this

First Day of July 1980

[SEAL]

Attest:

SIDNEY A. DIAMOND

Attesting Officer          Commissioner of Patents and Trademarks